United States Patent [19]

Maglio

[11] E Patent Number: Re. 33,670

[45] Reissued Date of Patent: Aug. 20, 1991

[54] GRANULAR PESTICIDE COMPOSITION

[75] Inventor: Michael J. Maglio, Glenolden, Pa.

[73] Assignee: ATOCHEM North America, Inc., Philadelphia, Pa.

[21] Appl. No.: 716,051

[22] Filed: Mar. 26, 1985

Related U.S. Patent Documents

Reissue of:

[64] Patent No.: 4,440,746
Issued: Apr. 3, 1984
Appl. No.: 437,381
Filed: Oct. 28, 1982

[51] Int. Cl.[5] ..... A01N 25/12; A61K 9/16; B01J 13/20

[52] U.S. Cl. ..... 424/408; 424/78; 424/486; 428/402.24; 514/64; 514/951; 514/965

[58] Field of Search ..... 424/78, 486, 408; 428/402.24; 514/64, 951, 965

[56] References Cited

U.S. PATENT DOCUMENTS

| | | | |
|---|---|---|---|
| 2,098,836 | 11/1937 | Ressler | 424/78 |
| 3,265,638 | 8/1966 | Goodman et al. | 252/518 |
| 4,110,431 | 8/1978 | Oita | 424/78 |
| 4,439,488 | 3/1984 | Trimnell et al. | 428/402.24 |

FOREIGN PATENT DOCUMENTS

| | | | |
|---|---|---|---|
| 1222016 | 2/1971 | United Kingdom | 264/4.1 |

*Primary Examiner*—Richard D. Lovering

[57] ABSTRACT

A granular pesticide composition is prepared by reacting polyvinyl alcohol, pesticide, a borate, and optional filler(s) in water until a gel is formed, drying the gel, and then grinding the product to the desired particle size. The product is then applied to the soil for controlling pests.

6 Claims, No Drawings

GRANULAR PESTICIDE COMPOSITION

Matter enclosed in heavy brackets [ ] appears in the original patent but forms no part of this reissue specification; matter printed in italics indicates the additions made by reissue.

*This is an application for reissue of U.S. Pat. No. 4,440,746 granted Apr. 3, 1985.*

BACKGROUND OF THE INVENTION

This invention relates to a composition and method of treating the soil with a slow release matrix-carried pesticide for controlled, sustained release of active agents contained within the matrix to protect plants from damage by various pests. More particularly, the invention comprehends the use of a polyvinyl alcohol (PVA)-borate based release system for pesticides applied to the soil. U.S. Pat. No. 4,110,431 discloses the use of polyvinyl alcohol-borate complexes formed by water activation of mixtures of the PVA and borax in situ for attaching plant treatment additives to plane foliage. Japanese Patent No. 74/48073 describes the use of borax to harden PVA used in the form of micro-capsules to encapsulate perfume and flame retardants. South African Patent Nos. 69/00122 and 69/00088 teach the use of PVA-borate capsules for plasticizers and dyes.

SUMMARY OF THE INVENTION

The present invention is directed to a granular, slow release matrix-carried pesticide prepared by reacting an aqueous solution of polyvinyl alcohol and the desired pesticide plus optional filler(s) with a borate with agitation until the reaction is complete forming a gel, drying the gel, and grinding the dried product to the desired particle size. This produce is then applied to the soil where it slowly releases the pesticide for controlling the desired pest.

DETAILED DESCRIPTION OF THE INVENTION

The present invention requires a water soluble polyvinyl alcohol, a borate, and optional filler(s). When the pesticide-containing polyvinyl alcohol solution and the borate are combined, they form a didiol complex, as indicated below:

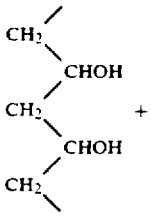

-continued

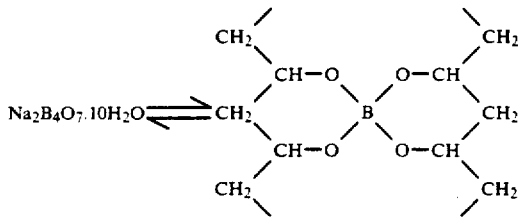

The reaction mixture thereby gels and entraps the pesticide in a matrix. The matrix is freed from water by drying, and then further refined by grinding and screening to the desired particle size. Granulates in the 14–40 mesh range are preferred.

Any pesticide which is compatible with the matrix can be employed for the present invention. Typical examples are chlorpyrifos, chlorpyrifos-methyl, methyl parathion, parathion, diazinon, fonofos, fensulfothion, phorate, trifluralin, etc., which can be used undiluted, in the form of suited solutions, on fillers, or in combinations.

As far as polyvinyl alcohol is concerned, any water soluble grade can be used in the practice of this invention. Suited typical commercial products are the various partially or fully hydrolyzed polyvinyl acetates sold in various molecular weight ranges under the trade names of Gelvatol, Vinol, Elvanol, etc. Preferred are products which are characterized by high solubility/low viscosity in water.

For effecting gelation of PVA, various sources of borate ions can be used. Suited materials are alkali metal, alkaline earth metal and ammonium salts of borate anions such as tetraborate and metaborate anions. Examples are sodium borate (borax), sodium metaborate, and potassium borate. Also combinations of boric acid and alkalizing agents are effective.

With respect to optional filler(s), a large variety of powdered or granular materials can be employed in the practice of this invention. Examples are various diatomites, attapulgites, bentonites, talcs, montmorillonites, perlites, vermiculites, calcium carbonates, corn cob grits, wood flour, lignin sulfonates, etc.

The amounts of the various ingredients in the total formulation can vary widely, and range from about 5–90% (by weight) of PVA, 2–50% of the active ingredient(s), 0–80% of the filler(s), and 1–20% of borate. Preferred ranges are: 5–70% of PVA, 5–30% of active ingredient(s), and 30–80% of filler(s). The amount of borate required to effect gelation varies with the type and amount of PVA and filler(s) used in the particular formulation and is best determined experimentally.

EXAMPLE I

Twenty grams of PVA (marketed by the Monsanto Corporation under the tradename Gelvatol 9000) were dissolved in 180 grams of deionized water to yield 200 grams of a 10% PVA solution. Ten grams of a technical grade methyl parathion (76% active) was dispersed in the 10% PVA solution. Twenty-one grams of a 10% sodium borate (borax) in water solution was then added to the PVA-methyl parathion dispersion and reacted with stirring until an opaque gel formed. The PVA-methyl parathion gel was dried in a forced air oven at 55° C. for 16 hours, yielding 29.7 grams of product. The dried product was then ground in a blender to a particle size that would pass through a number 14 mesh screen but remained on a number 40 mesh screen. This particulate material was found to contain 25.1% active ingredient.

EXAMPLE II

Eight grams of Gelvatol 9000 were dissolved in 72 grams deionized water yielding 80 grams of a 10% PVA solution. Into this 5 grams of Dursban XM (a commercial chlorpyrifos at 65% active ingredient) was dispersed. Three grams of sodium borate (borax) were then dissolved in 15 grams of water and added to the PVA-Dursban XM dispersion and reacted until a gel precipitate formed. This gel precipitate was then dried in an exhaust hood for 24 hours to yield 14.2 grams of product. The dried product was then ground to a particle size that would pass through a number 14 mesh screen but yet remained on a number 40 mesh screen. The granular product was found to contain 14.5% active ingredient.

EXAMPLE III

Five grams of Gelvatol 9000 were dissolved in 45 grams deionized water. To this solution 19.0 grams of methyl parathion-loaded Diatomite [prepared by soaking 13.5 grams of Celatom MN-39 (Eagle Pitcher) with 4.5 grams technical methyl parathion in ~40 grams methylene chloride, and removing volatile components at ~50° C./130 mm Hg] were added, followed by dropwise addition of 5 grams of warm 10% borax solution. The resulting gel was dried in an exhaust hood for 24 hours, and then in an oven at ~75° C. for 2½ hours. The dry product (23.4 grams) was ground in a blender and then classified to yield 14.3 grams product of 14–40 mesh size. It contained 13.2% active ingredient.

EXAMPLE IV

The granular product of Example I was tested in a laboratory soil bioassay using 3 day oid housefly larvae as test organisms. Twenty-five housefly larvae were exposed to soil at intervals of 3, 10, 17, 38, and 45 days following treatment with the granular product and the number of adult flies emerging from the soil was counted. The granular product was used at a rate equivalent to ½ pound of active ingredient per acre applied in 6" bands spaced 40" apart.

For the sake of comparison, a commercial formulation of methyl parathion was also tested at the same level of active ingredient and the results of both products were recorded in Table I. % Control is defined as the percent reduction in adult housefly emergence.

TABLE I

| | % Control | | | | |
|---|---|---|---|---|---|
| | 3 | 10 | 17 | 38 | 45 |
| PVA Matrix | 39.0 | 93.8 | 91.9 | 65.3 | 76.4 |
| Methyl Parathion EC | 21.0 | 10.4 | 14.9 | 3.9 | 0.0 |
| Control | 0.0 | 4.0 | 1.3 | 10.7 | 23.4 |

EXAMPLE V

The granular product of Example II was then tested for bioactivity in soil as in Example IV.

For the sake of comparison, a commercial formulation of chlorpyrifos (Lorsban® 15G) was tested. The results of both products were recorded in Table II as follows:

TABLE II

| | % Control | | | | |
|---|---|---|---|---|---|
| | 3 | 10 | 17 | 24 | 31 |
| PVA Matrix | 97.9 | 98.0 | 96.9 | 80.7 | 75.0 |
| Lorsban 15G | 91.4 | 96.0 | 96.9 | 68.6 | 39.6 |
| Control | 6.7 | 0.0 | 4.0 | 1.3 | 6.0 |

EXAMPLE VI

In the laboratory soil bioassay with 3 day old housefly larvae, the product of Example III showed the following activity as compared to the methyl parathion-loaded filler without PVA matrix:

TABLE III

| | % Control | | | |
|---|---|---|---|---|
| | 3 | 17 | 31 | 45 |
| PVA Matrix | 84.3 | 60.9 | 74.0 | 72.0 |
| MP-loaded Filler | 94.8 | 57.9 | 54.0 | 0 |
| Control | 4.0 | 2.7 | 0 | 10.7 |

As evident, the PVA matrix formulation exhibited a much longer-lasting insecticidal activity than a comparable formulation without the matrix.

What is claimed:

1. A granular slow release soil pesticide composition *comprising by weight based on the total composition of from about 5 to about 90% of polyvinyl alcohol, from about 1 to about 20% of a borate, from about 2 to about 50% of a compatible pesticide, and 0 to about 80% of filler(s)* prepared by mixing [from about 5 to about 90% by weight of] (*a*) an aqueous solution of polyvinyl alcohol *wherein the solids concentration of polyvinyl alcohol is about 10%* and [from about 2 to about 50% of] a compatible pesticide [plus 0 to about 80% of] *and optionally* at least one filler selected from the class consisting of diatomites, attapulgites, bentonites, talcs, montmorillonites, perlites, vermiculites, calcium carbonates, corn cob grits, wood flour, lignin sulfonates, and mixtures thereof with [from about 1 to about 20% of] (*b*) a borate until [said] ingredients (*a*) *and* (*b*) react to form a gel, drying the gel, and grinding the dried product to the desired particle size.

2. The composition of claim 1 wherein the pesticide is selected from the group consisting of chlorpyrifos, chlorpyrifos-methyl, diazinon, fonofos, parathion, fensulfothion, methyl parathion, phorate, and trifluralin.

3. The composition of claim 1 wherein the product is ground to pass through a number 14 mesh screen but is retained on a number 40 mesh screen.

4. A method of controlling pests comprising applying an effective amount of the composition of claim 1 to soil.

*5. A method of encapsulating a pesticide comprising the steps of:*

*a. preparing a solution or dispersion of such pesticide in a matrix-forming material comprising an aqueous solution of a gel-forming polyvinyl alcohol wherein said aqueous solution has a solids concentration of said polyvinyl alcohol of about 10%, wherein the relative amount of said polyvinyl alcohol with respect to said pesticide is sufficient to entrap said pesticide within a matrix of said polyvinyl alcohol;*

*b. reacting said polyvinyl alcohol with a borate to form a continuous insolubilized matrix gel having entrapped therein uniformly dispersed, discontinuous domains of said pesticide; and*

*c. recovering free-flowing particles of said entrapped pesticide.*

*6. A composition of matter produced by the process of claim 5.*

* * * * *